United States Patent [19]

Treuner

[11] Patent Number: 4,680,409
[45] Date of Patent: Jul. 14, 1987

[54] HYDRAZIDE CONTAINING DERIVATIVES OF 2-AMINO-4-THIAZOLE-ACETIC ACID

[75] Inventor: Uwe D. Treuner, Regensburg, Fed. Rep. of Germany

[73] Assignee: E. R. Squibb & Sons, Inc., Princeton, N.J.

[21] Appl. No.: 812,658

[22] Filed: Dec. 23, 1985

Related U.S. Application Data

[62] Division of Ser. No. 658,849, Oct. 9, 1984, Pat. No. 4,610,824.

[51] Int. Cl.$^4$ .......................................... C07D 277/40
[52] U.S. Cl. ...................................... 548/194; 546/209
[58] Field of Search ........................ 548/194; 546/209

[56] References Cited

U.S. PATENT DOCUMENTS

| | | | |
|---|---|---|---|
| 4,252,802 | 2/1981 | Denzel et al. | 544/22 |
| 4,487,937 | 12/1984 | Heymes | 548/194 |
| 4,525,473 | 6/1985 | Aburaki et al. | 544/22 |

FOREIGN PATENT DOCUMENTS

| | | | |
|---|---|---|---|
| 0162394 | 5/1985 | European Pat. Off. | 544/22 |
| 2071650 | 9/1981 | United Kingdom . | |

Primary Examiner—Robert Gerstl
Attorney, Agent, or Firm—Lawrence S. Levinson; Donald J. Barrack

[57] ABSTRACT

Compounds having the formula

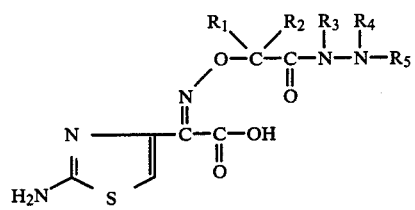

wherein
$R_1$ and $R_2$ are each independently hydrogen or alkyl of 1 to 4 carbon atoms, or $R_1$ and $R_2$ together with the carbon atom to which they are attached form a cycloalkyl ring;
$R_3$ is hydrogen or alkyl;
$R_4$ is hydrogen or alkyl, and $R_5$ is hydrogen, alkyl, phenyl, substituted phenyl, a 4,5,6 or 7-membered heterocycle, phenylalkyl, (substituted phenyl)alkyl, (4,5,6 or 7-membered heterocycle)alkyl,

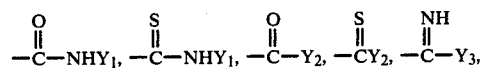

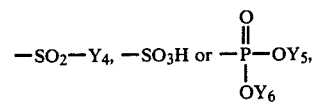

or together $R_4$ and $R_5$ are $=CH-Y_7$; wherein $Y_1$ is hydrogen, alkyl, phenyl, substituted phenyl, methylcarbonyl, trifluoromethylcarbonyl, phenylcarbonyl, (substituted phenyl)carbonyl, carboxymethyl, methylsulfonyl, phenylsulfonyl, (substituted phenyl)sulfonyl, aminocarbonyl, aminocarbonylamino, aminoethyl, hydroxy, alkoxy, amino, alkylamino, dialkylamino, phenylcarbonylamino, (substituted phenyl)carbonylamino, 1-pyrrolidinyl or 1-piperidinyl; $Y_2$ is hydrogen, alkyl, phenyl, substituted phenyl, a 4,5,6 or 7-membered heterocycle, alkoxy, formyl, carbonyl, aminocarbonyl, aminothiocarbonyl, methylaminocarbonyl, methylaminothiocarbonyl, trifluoromethyl, phenylmethyl, (substituted phenyl)methyl, phenyloxymethyl, (substituted phenyl)oxymethyl, cyanomethyl, hydroxymethyl, alkoxymethyl, aminomethyl, methylcarbonylaminomethyl, aminocarbonylaminomethyl, methylsulfonylaminomethyl, carboxymethyl, aminocarbonylmethyl, alkoxycarbonylmethyl, (4,5,6 or 7-membered heterocycle)-alkyl, hydroxyaminocarbonylmethyl, or azidomethyl; $Y_3$ is amino, alkyl, alkylthio, carboxythio, alkoxycarbonylthio or aminocarbonylthio; $Y_4$ is alkyl, amino, hydroxyamino, alkoxyamino, methylcarbonylamino, or phenylcarbonylamino; $Y_5$ is hydrogen or alkyl; $Y_6$ is hydrogen, alkyl, carboxymethyl, or aminocarbonylmethyl; and $Y_7$ is phenyl or substituted phenyl;

are useful chemical intermediates for the preparation of $\beta$-lactam antibiotics.

4 Claims, No Drawings

HYDRAZIDE CONTAINING DERIVATIVES OF 2-AMINO-4-THIAZOLE-ACETIC ACID

BACKGROUND OF THE INVENTION

This is a division of application Ser. No. 658,849, filed Oct. 9, 1984, now U.S. Pat. No. 4,610,824, issued Sept. 9, 1986.

U.S. Pat. No. 4,252,802, issued Feb. 24, 1981, describes cephalosporin antibiotics having a 7-acylamino group of the formula

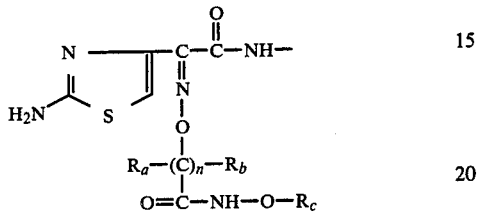

wherein $R_a$ and $R_b$ are each independently hydrogen or methyl, $R_c$ is hydrogen, alkyl, phenyl or alkyl; and n is 1, 2, 3, or 4. The cephalosporins described by the reference are antibacterial agents.

United Kingdom patent application No. 2071650, published Sept 23, 1981, describes monocyclic β-lactam antibiotics having a sulfonic acid salt substituent in the 1-position of the β-lactam nucleus and an acylamino substituent in the 3-position of the β-lactam nucleus.

BRIEF DESCRIPTION OF THE INVENTION

Compounds having the formula

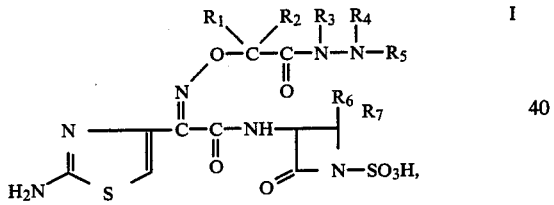

and pharmaceutically acceptable salts thereof, have antibacterial activity. In formula I, and throughout the specification, the symbols are as defined below.

$R_1$ and $R_2$ are each independently hydrogen or alkyl of 1 to 4 carbon atoms, or $R_1$ and $R_2$ together with the carbon atom to which they are attached form a cycloalkyl ring;

$R_3$ is hydrogen or alkyl;

$R_4$ is hydrogen or alkyl, and $R_5$ is hydrogen, alkyl, phenyl, substituted phenyl, a 4,5,6 or 7-membered heterocycle (hereinafter referred to as $R_x$), phenylalkyl, (substituted phenyl)alkyl, $R_x$-alkyl,

[wherein $Y_1$ is hydrogen, alkyl, phenyl, substituted phenyl, methylcarbonyl, trifluoromethylcarbonyl, phenylcarbonyl, (substituted phenyl)carbonyl, carboxymethyl, methylsulfonyl, phenylsulfonyl, (substituted phenyl)sulfonyl, aminocarbonyl, aminocarbonylamino, aminoethyl, hydroxy, alkoxy, amino, alkylamino, dialkylamino, phenylcarbonylamino, (substituted phenyl)carbonylamino, 1-pyrrolidinyl, or 1-piperidinyl],

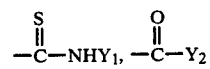

[wherein $Y_2$ is hydrogen, alkyl, phenyl, substituted phenyl, $R_x$, alkoxy, formyl, carbonyl, aminocarbonyl, aminothrocarbonyl, methylaminocarbonyl, methylaminothrocarbonyl, trifluoromethyl, phenylmethyl, (substituted phenyl)methyl, phenyloxymethyl, (substituted phenyl)oxymethyl, cyanomethyl, hydroxymethyl, alkoxymethyl, aminomethyl, methylcarbonylaminomethyl, aminocarbonylaminomethyl, methylsulfonylaminomethyl, carboxymethyl, aminocarbonylmethyl, alkoxycarbonylmethyl, $R_x$-alkyl, hydroxyaminocarbonylmethyl, or azidomethyl],

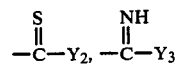

[wherein $Y_3$ is amino, alkyl, alkylthio, carboxythio, alkoxycarbonylthio, or amino carbonythio], —SO$_2$-Y$_4$ [wherein $Y_4$ is alkyl, amino, hydroxyamino, alkoxyamino, methylcarbonylamino, or phenylcarbonylamino],

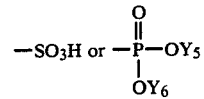

[wherein $Y_5$ is hydrogen or alkyl and $Y_6$ is hydrogen, alkyl, carboxymethyl, or aminocarbonylmethyl]; or together $R_4$ and $R_5$ are =CH-Y$_7$ wherein $Y_7$ is phenyl or substituted phenyl;

$R_6$ and $R_7$ are the same or different and each is hydrogen, alkyl, alkenyl, alkynyl, cycloalkyl, phenyl, substituted phenyl or $R_x$, or one of $R_6$ and $R_7$ is hydrogen and the other is azido, halomethyl, diahalomethyl, trihalomethyl, alkoxycarbonyl, 2-phenylethenyl, 2-phenylethynyl, carboxyl, —CH$_2$X$_1$ [wherein $X_1$ is azido, amino ('NH$_2$), hydroxy, alkanoylamino, phenylcarbonylamino, (substituted phenyl)carbonyl- amino, alkylsulfonyloxy, phenylsulfonyloxy, (substituted phenyl)sulfonyloxy, phenyl, substituted phenyl, cyano,

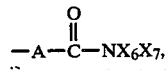

—S—X$_2$, or —O—X$_2$ (wherein A, X$_2$, X$_6$ and X$_7$ are as hereinafter defined)], —S—X$_2$ or —O—X$_2$ [wherein X$_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl],

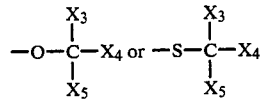

[wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl

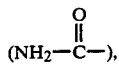

(substituted amino)carbonyl, or cyano (—C≡N)], or

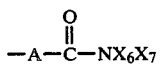

(wherein A is —CH=CH—, —(CH$_2$)$_n$—, —CH$_2$—O—, —CH$_2$—NH—, or —CH$_2$—S—CH$_2$—, n is 0, 1 or 2, and $X_6$ and $X_7$ are the same or different and each is hydrogen, alkyl, phenyl, or substituted phenyl, or $X_6$ is hydrogen and $X_7$ is amino, substituted amino, alkanoylamino or alkoxy, or $X_6$ and $X_7$ when taken together with the nitrogen atom to which they are attached form a 4, 5, 6 or 7-membered heterocycle).

Listed below are definitions of various terms used to describe β-lactams of this invention. These definitions apply to the terms as they are used throughout the specification (unless they are otherwise limited in specific instances) either individually or as a part of a larger group.

The terms "alkyl" and "alkoxy" refer to both straight and branched chain groups. Those groups having 1 to 10 carbon atoms are preferred.

The term "cycloalkyl" refers to cycloalkyl groups having 3, 4, 5, 6 or 7 carbon atoms.

The term "substituted alkyl" refers to alkyl groups substituted with one, or more, azido, amino (—NH$_2$), halogen, hydroxy, carboxy, cyano, alkoxycarbonyl, aminocarbonyl, alkanoyloxy, alkoxy, phenyloxy, (substituted phenyl)oxy, $R_x$-oxy, mercapto, alkylthio, phenylthio, (substituted phenyl)thio, alkylsulfinyl, or alkylsulfonyl groups.

The terms "alkanoyl", "alkenyl", and "alkynyl" refer both to straight and branched chain groups. Those groups having 2 to 10 carbon atoms are preferred.

The terms "halogen" and "halo" refer to fluorine, chlorine, bromine and iodine.

The term "substituted phenyl" refers to a phenyl group substituted with 1, 2 or 3 amino (—NH$_2$), halogen, hydroxyl, trifluoromethyl, alkyl (of 1 to 4 carbon atoms), alkoxy (of 1 to 4 carbon atoms), or carboxyl groups.

The expression "a 4, 5, 6, or 7-membered heterocycle" (referred to as "$R_x$") refers to substituted and unsubstituted, aromatic and non-aromatic groups containing one or more nitrogen, oxygen or sulfur atoms. Exemplary substituents are oxo (=O), halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino

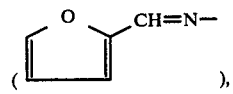

and substituted alkyl groups (wherein the alkyl group has 1 to 4 carbons). One type of "4,5,6 or 7-membered heterocycle" is the "heteroaryl" group. The term "heteroaryl" refers to those 4,5,6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetinyl, oxetanyl, thietanyl, piperidinyl, piperazinyl, imidazolidinyl, oxazolidinyl, pyrrolidinyl, tetrahydropyrimidinyl, dihyrothiazolyl and hexahydroazepinyl. Exemplary of the substituted 4,5,6 or 7-membered heterocycles are 1-alkyl-3-azetinyl, 2-oxo-1-imidazolidinyl, 3-alkylsulfonyl-2-oxo-1-imidazolidinyl, 3-benzylimino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)-amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula —NZ$_1$Z$_2$ wherein Z$_1$ is hydrogen, alkyl, phenyl, substituted phenyl, phenylalkyl or (substituted phenyl)alkyl, and Z$_2$ is alkyl, phenyl, substituted phenyl, phenylalkyl, (substituted phenyl)alkyl, hydroxy, cyano, alkoxy, phenylalkoxy, or amino (—NH$_2$).

The terms "salt" and "salts", when used to describe the β-lactams of this invention, refer to basic salts formed with inorganic and organic bases. Such salts include ammonium salts, alkali metal salts like sodium and potassium salts, alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. Pharmaceutically acceptable salts are preferred.

Salts of an azetidinone-1-sulfonic acid are formed by reacting the free acid form of the sulfonate with one or more equivalents of an appropriate base providing the desired cation in water or in a solvent mixture containing water. The salt is isolated by removal of solvent in vacuo, or, in the case of water, by lyophilization. The free acid of the sulfonate is formed by treating an azetidinone-1-sulfonic acid salt with an insoluble sulfonic acid such as a cation exchange resin in the hydrogen form (e.g. a polystyrene sulfonic acid resin like Dowex 50).

Alternatively, salts may be formed by cation interchange. A salt of a β-lactam compound soluble in organic solvent is combined with a salt containing the desired cation, also soluble in the same solvent system. The solvent system is chosen so that the formed salt is much less soluble than either of the added salts and thus precipitates from the medium and is collected.

DETAILED DESCRIPTION OF THE INVENTION

The β-lactams of formula I, and pharmaceutically acceptable salts thereof, have activity against gram-negative organisms. The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals, a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with β-lactams of this invention. Such methods of administration include oral, intravenous, intramuscular, and as a suppository.

The compounds of this invention can be prepared using a variety of procedures. One method utilizes as a starting material the known monocyclic β-lactam antibiotics having the formula

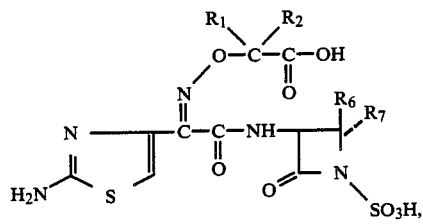

and salts thereof. Compounds of formula II are described in the literature; see, for example, United Kingdom patent application No. 2071650, published Sept. 23, 1981. Reaction of a compound of formula II with a hydrazide having the formula

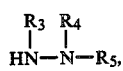

or a salt thereof, in the presence of a coupling agent, yields the desired products of formula I. If the starting material of formula II is an inner salt (—SO₃H in the 1-position), it is preferable to first treat the compound with one equivalent of a base (e.g., tributylamine or trioctylamine) to form the salt of the sulfonic acid. Preferably, the reaction is run in the presence of a substance capable of forming a reactive intermediate in situ, such as N-hydroxybenzotriazole and/or a catalyst such as dimethylaminopyridine, using a coupling agent such as dicyclohexylcarbodiimide. Exemplary solvents which can be used for the reaction are dimethylformamide, tetrahydrofuran, dichloromethane or mixtures thereof.

Alternatively, the comounds of this invention can be prepared by acylating a compound having the formula

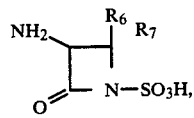

or a salt thereof, with a carboxylic acid having the formula

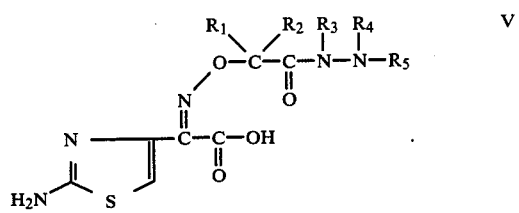

Well-known acylation procedures can be used for the reaction. Exemplary techniques include the use of a carboxylic acid of formula V or a corresponding carboxylic acid halide or carboxylic acid anhydride. The reaction with a carboxylic acid proceeds most readily in the presence of a carbodiimide such as dicyclohexylcarbodiimide and a substance capable of forming a reactive intermediate is situ such as N-hydroxybenzotriazole or N-hydroxysuccinimide.

Compounds of formula V are novel compounds, and as such, form an integral part of this invention. They can be prepared by reacting (2-amino-4-thiazolyl)-glyoxylic acid, which has the formula

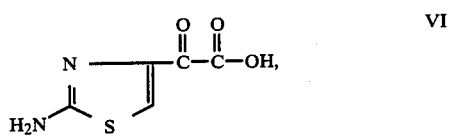

with a compound having the formula

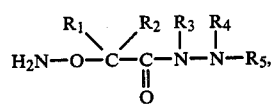

or a salt thereof. The reaction proceeds best in water and in mixtures of water and organic solvents, such as methanol, ethanol, tetrahydrofuran or dioxane.

Reactants of formula VII can be prepared by reacting a compound having the formula

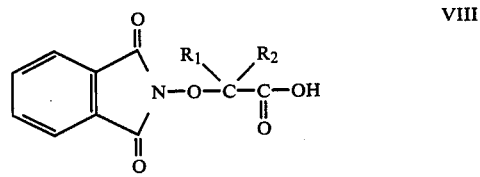

or

-continued

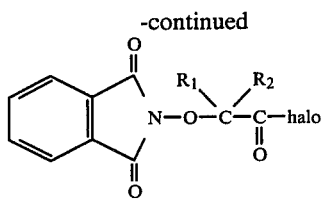

with hydrazide having the formula

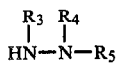

to yield the corresponding compound having the formula

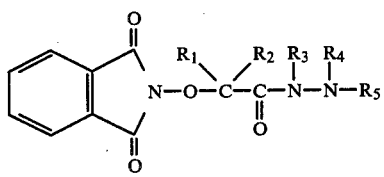

If an acid reactant of formula VIII is used, a suitable coupling agent, such as dicyclohexylcarbodiimide, should be present. Alternatiely, an acid of formula VIII can be activated by formation of mixed anhydride. If an acid halide derivative of formula IX is used, a suitable base should be present. The hydrazides of formula X can be deprotected using standard methodology to yeild the desired reactants of formula VII. Exemplary deprotecting agents are hydrazine and methylhydrazine.

Hydrazine derivatives of formula II, and methods for their preparation, are well known in the literature. Reviews of their synthesis can be found in Smith, "The Chemistry of Open-Chain Organic Nitrogen Compounds", Vols. I and II, Benjamin, Inc., New York, Amsterdam, 1966; Muller, "Methoden der Organischen Chemie" (Houben-Weyl), Vol. 10/2, Georg Thieme Verlag Stuttgart, 1967; Sandler and Karo, "Organic Functional Group Preparations", Vol. 1, Academic Press, New York, 1968; and Timberlake and Stowell, "The Chemistry of Hydrazo, Azo, and Azoxy Groups", ed. S. Patai, part 1, Interscience, New York, 1975.

Reactants of formula IV are described in United Kingdom patent application No. 2071650, published Sept. 23, 1981.

The compounds of this invention (both the pharmaceutical products of formula I and the intermediates of formula V) contain an imino group

and can exist as syn or anti isomers or as mixtures of both. All of these isomeric forms are within the scope of this invention. The syn isomers are preferred, however, because that isomeric form has superior activity.

Whether the pharmaceutical products of formula I are prepared from a starting compound of formula II or from a starting compound of formula V, the isomerism of the starting material will determine the isomerism of the product. In preparing a compound of formula V, the ratio of syn/anti will depend on the reaction conditions. If the reaction of compounds of formula VI and VII is run at room temperature, the ratio of syn/anti will be favorable to the obtaining of the syn isomer. Lowering the reaction temperature increases the ratio of syn/anti, but slows the reaction. Raising the reaction temperature decreases the ratio of syn/anti, but speeds the reaction. Separation of the syn and anti isomers can be accomplished using fractional crystallization.

Alternative methodology for preparing the compounds of this invention will be apparent to the practitioner of this ivention. For example, those compounds of formula I wherein $R_4$ and $R_5$ are $=CH-Y_7$ can be prepared by reacting the corresponding compound of formula I wherein $R_4$ and $R_5$ are each hydrogen with the appropriate benzaldehyde.

The following examples are specific embodiments of this invention.

EXAMPLE 1

[3S-[3α(Z),4β]]-3-[[(2-Amino-4-thiazolyl)[[1,1-dimethyl-2-[2-[(1,1-dimethylethoxy)carbonyl]-hydrazino]-2-oxoethoxy]imino]acetyl]amino]-4-methyl-2-oxo-1-azetidinesulfonic acid, monopotassium salt

[3S-[3α(Z),4β]]-3-[[(2-Amino-4-thiazolyl)-[(1-carboxy-1-methylethoxy)imino]acetyl]amino]-4-methyl-2-oxo-1-azetidinesulfonic acid (2.18 g), 0.93 g of tributylamine, 0.1 g of N-hydroxybenzotriazole and 0.05 g of dimethylaminopyridine were dissolved in 30 ml of dimethylformamide, and 1.06 g of N,N-dicyclohexylcarbodiimide was added. After stirring for 30 minutes, a solution of 0.66 g of [(1,1-dimethylethoxy)carbonyl]hydrazine in 5 ml of dimethylformamide was added. Stirring overnight at room temperature, filtering off the formed dicyclohexylurea and distilling off the solvent yielded an oily residue which was dissolved in acetone (30 ml) and filtered. To the filtrate were added 30 ml of ether and a solution of 1.7 g of potassium perfluorobutanesulfonate in 10 ml of acetone. Crude product (1.8 g) was obtained as a precipitate. Purification was by column chromatography on HP-20*, using water and water/tetrahydrofuran (9:1) as eluents, and yielded 1.3 g of the title compound, melting point 258° C.

*HP-20: macroreticular styrene-divinylbenzene copolymer, Mitsubishi Chemical Industries, Ltd.

IR (KBr): 1765 cm$^{-1}$ (β-lactam carbonyl)

$^1$H-NMR (200 MHz, DMSO-d$_6$**): δ=1.38 (m, 15H); 3.68 (m,1H); 4.5 (dd, 1H); 6.78 (s,1H); 7.28 (s, broad, 2H); 8.75 (s, broad 1H); 9.13 (s, broad, 1H); 9.28 (d, broad, 1H) ppm.

**DMSO-d$_6$: deuterated dimethylsulfoxide

EXAMPLE 2

[3S-[3α(Z),4β]]-3-[[[[2-[2-Aminocarbonyl)hydrazino]-1,1-dimethyl-2-oxoethyl]imino](2-amino-4-thiazolyl)-acetyl]amino]-4-methyl-2-oxo-1-azetidinesulfonic acid, monopotassium salt

[3S-[3α(Z),4β]]-3-[[(2-Amino-4-thiazolyl)-[(1-carboxy-1-methylethoxy)imino]acetyl]amino]-4-methyl-2-oxo-1-azetidinesulfonic acid (2.18 g) and 0.93 g of tributylamine in 20 ml of dimethylformamide were stirred at room temperature and 0.1 g of N-hydroxybenzotriazole and 0.05 g of dimethylaminopyradine were added followed by 1.06 g of N,N-dicyclohexylcarbodiimide in 5 ml of dimethylformamide. After stirring for 30 minutes, a solution of 0.6 g of (aminocarbonyl)hydrazine, hydrochloride and 0.93 g of tributylamine in 15 ml of dimethylformamide were added. Stirring at room temperature overnight, filtering off the formed dicyclohexylurea and evaporating the dimethylformamide of the filtrate yielded a residue which was dissolved in 30 ml of acetone/tetrahydrofuran (1:1) and filtered. After adding 3.4 g of potassium perfluorobutanesulfonate in 15 ml of acetone, the filtrate formed a precipitate of 2.7 g crude product. This was purified by column chromatography on HP-20, using water as eluent, and yielding 1.3 g of the title compound, melting point 245° C., after freeze drying.

IR (KBR): 1763 cm$^{-1}$ ($\beta$-lactam carbonyl)

$^1$H-NMR (200 MHz, DMSO-d$_6$): $\delta$=1.38 (d, 6H); 1.40 (d, 3H); 3.65 (m, 1H); 4.53 (dd, 1H); 5.98 (s, broad, 2H); 6.80 (s, 1H); 7.23 (s, broad, 2H); 7.75 (s, 1H); 9.25 (d, 2H); 9.35 (s, 1H) ppm.

EXAMPLE 3

[3S-[3$\alpha$(Z),4$\beta$]]-3-[[(2-Amino-4-thiazolyl)[[2-[2-(aminothioxomethyl)hydrazino-1-dimethyl-2-oxoethoxy]imino]acetyl]amino]-4-methyl-2-oxo-1-azetidinesulfonic acid, monopotassium salt

[3S-[3$\alpha$(Z),4$\beta$]]-3-[[(2-Amino-4-thiazolyl)-[(1-carboxy-1-methylethoxy)imino]acetyl]amino]-4-methyl-2-oxo-1-azetidinesulfonic acid (2.18 g), 0.93 g of tributylamine, 0.1 g of N-hydroxybenzotriazole and 0.05 g of dimethylaminopyridine were dissolved in 30 ml of dimethylformamide and 1.06 g of N,N-dicyclohexylcarbodiimide in 5 ml of dimethylformamide was added. After stirring for 15 minutes at room temperature, 0.46 g of (aminothioxomethyl)hydrazine in 10 ml of dimethylformamide was added and stirring was continued for 6 hours. Formed dicyclohexylurea (0.98 g) was filtered off and the dimethylformamide of the filtrate was distilled off in vacuo. The oily residue was diossolved in 50 ml of acetone, filtered and after adding a solution of 1.7 g of potassium perfluorobutanesulfonate in 10 ml of acetone, crude product separated from the solution. It was washed with ether and purified by column chromatography on HP-20 using water as eluent and yielding 1.3 g of the title compound, melting point 215° C. (dec).

IR (KBr): 1765 cm$^{-1}$ ($\beta$-lactam carbonyl)

$^1$HR-NMR (200 MHz, DMSO-d$_6$): $\delta$=1.35 (s, 6H); 1.40 (d, 3H); 3.63 (m, 1H); 4.52 (dd, 1H); 6.80 (s, 1H); 6.95 (s, 1H); 7.30 (s, broad, 2H); 8.00 (s, 1H); 9.18 (d, 1H); 9.38 (s, 1H); 9.68 (s, 1H) ppm.

EXAMPLE 4

[3S-[3$\alpha$(Z),4$\beta$]]-3-[[[2-(2-Acetylhydrazino)-1,1-dimethyl-2-oxoethoxy]imino](2-amino-4-thiazolyl)-acetyl]amino]-4-methyl-2-oxo-1-azetidinesulfonic acid, monopotassium salt

[3S-[3$\alpha$(Z),4$\beta$]]-3-[[(2-Amino-4-thiazolyl)-[(1-carboxyl-1-methylethoxy)imino]acetyl]amino]-4-methyl-2-oxo-1-azetidinesulfonic acid (2.18 g) and 0.93 g of tributylamine were dissolved in 20 ml of dimethylformamide and stirred at room temperature. N-Hydroxybenzotriazole (0.1 g) and 0.05 g of dimethylaminopyridine were added followed by a solution of 1.06 g of N,N-dicyclohexylcarbodiimide in 10 ml of dimethylformamide. After 20 minutes stirring, a solution of 0.3 g of acetylhydrazine in 5 ml of dimethylformamide was added. After 5 hours, the formed dicyclohexylurea was filtered off and the dimethylformamide of the filtrate was distilled off in vacuo. The oily residue was dissolved in 30 ml of acetone, filtered and a solution of 1.7 g of potassium perfluorobutanesulfonate in 10 ml of acetone was added. Crude product (1.7 g) was obtained as a precipitate, washed with ether, dried and purified by column chromatography on HP-20 using water as an eluent and yielding 0.8 g of the title compound, melting point 241° C. (dec).

IR (KBr): 1760 cm$^{-1}$ ($\alpha$-lactam carbonyl)

$^1$H-NMR (200 MHz, DMSO-d$_6$): $\delta$=1.38 (s, 6H); 1.40 (d, 3H); 1.83 (s, 3H); 3.68 (m, 1H); 4.53 (dd, 1H); 6.80 (s, 1H); 7.28 (s, 2H); 9.15 (s, broad, 1H); 9.28 (d, 1H); 9.73 (s, broad, 1H) ppm.

EXAMPLE 5

[3S-[3$\alpha$(Z),4$\beta$]]-3-[[(2-Amino-4-thiazolyl)[[2-[2-(2-furanylcarbonyl)hydrazino]-1-dimethyl-2-oxoethoxy]imino]acetyl]amino]-4-methyl-2-oxo-1-azetidinesulfonic acid, monopotassium salt

[3S-[3$\alpha$(Z),4$\beta$]]-3-[[(2-Amino-4-thiazolyl)-[(1-carboxy-1-methylethoxy)imino]acetyl]amino]-4-methyl-2-oxo-1-azetidinesulfonic acid (2.18 g), 0.93 g of tributylamine, 0.1 g of N-hydroxybenzotriazole and 0.05 g of dimethylaminopyridine were dissolved in 30 ml of dimethylformamide. After adding 1.06 g of N,N-dicyclohexylcarbodiimide and stirring at room temperature for 20 minutes, a solution of 0.75 g of (2-furanylcarbonyl)hydrazine in 5 ml of dimethylformamide was added. Overnight stirring followed by filtering off the formed dicyclohexylurea and distilling of the dimethylformamide of the filtrate yielded an oily residue. It was dissolved in 50 ml of acetone, filtered and to the solution was added 1.7 g of potassium perfluorobutanesulfonate and 20 ml of ether yielding a precipitate of the crude product (2.4 g). Purification by HP-20 column chromatography using water as eluent yielded 1.5 g of the title compound, melting point 255° C. (dec).

IR (KBr): 1763 cm$^{-1}$($\alpha$-lactam carbonyl)

$^1$H-NMR (200 MNH, DMSO-d$_6$): $\delta$=1.45 (dd, 9H); 3.68 (m, 1H); 4.51 (dd, 1H); 6.60 (m, 1H); 6.85 (s, 1H); 7.23 (d, 1H); 7.28 (s, 1H); 7.85 (s, 1H); 9.31 (d, broad, 1H); 9.41 (s, broad, 1H); 10.25 (s, broad, 1H) ppm.

EXAMPLE 6

[3S-[3$\alpha$(Z),4$\beta$]]-3-[[(2-Amino-4-thiazolyl)[(2-(formylhydrazino)-1,1-dimethyl-2-oxoethoxy]-imino]acetyl]amino-4-methyl-2-oxo-1-azetidinesulfonic acid, monopotassium salt

[3S-[3$\alpha$(Z),4$\beta$]]-3-[[(2-Amino-4-thiazolyl)-[(1-carboxy-1-methylethoxy)imino]acetyl]amino]-4-methyl-2-oxo-1-azetidinsulfonic acid (1.09 g), 0.88 g of triocytlamine, 0.05 g of N-hydroxybenzotriazole and 0.025 g of dimethylaminopyridine were dissolved in 50 ml of tetrahydrofuran. After adding a solution of 0.55 g of N,N-dicyclohexylcarbodiimide in 10 ml of tetrahydrofuran and stirring for 30 minutes at room temperature, a solution of 0.15 g of formylhydrazine in 10 ml of tetrahydrofuran was added. Overnight stirring was followed by filtering off the formed dicyclohexylurea and the addition of 0.85 g of potassium perfluorobutanesulfonate to the filtrate to give crude product as a precipitate. This was recrystallized from methanol/isopropanol to give 0.9 g of the title compound, melting point 254° C. (dec).

IR (KBr): 1762 cm$^{-1}$ ($\beta$-lactam carbonyl)

$^1$H-NMR (200 MHz, DMSO-d$_6$): $\delta$=1.40 (dd, 9H); (m, 1H); 4.52 (dd, 1H); 6.58 (s, 1H); 7.30 (s, 2H); 8.03 (s, 1H); 9.25 (s, broad, 1H); 9.28 (d, broad, 1H); 9.90 (s, broad, 1H) ppm.

EXAMPLE 7

[3S-[3α(Z),4β]]-3-[[(2-Amino-4-thiazolyl)[[2-[2-[[(aminocarbonyl)amino]acetyl]hydrazino]-1,1-dimethyl-2-oxoethoxy]imino]acetyl]amino]-4-methyl-2-oxo-1-azetidinesulfonic acid, monopotassium salt

[3S-[3α(Z),4β]]-3-[[(2-Amino-4-thiazolyl)-[(1-carboxy-1-methylethoxy)imino]acetyl]amino]-4-methyl-2-oxo-1-azetidinesulfonic acid (1.09 g), 0.47 g of tributylamine, 0.05 g of N-hydroxybenzotriazole and 0.025 g of dimethylaminopyridine were dissolved in 30 ml of dimethylformamide. N,N-Dicyclohexylcarbodiimide (0.55 g) was added and, after stirring for 20 minutes, a solution of 0.35 g of [[(aminocarbonyl)amino]acetyl]hydrazine in 20 ml of dimethylformamide was added. Stirring overnight, filtering off the formed dicyclohexylurea and distilling off the dimethylformamide of the filtrate yielded a residue which was dissolved in 30 ml of tetrahydrofuran/methanol (2:1) and filtered. To the filtrate was added a solution of 0.85 g of potassium perfluorobutanesulfonate in 10 ml of acetone. Crude product was obtained as a precipitate (1.3 g). Purification by column chromatography on HP-20 using water as an eluent yielded the title compound, melting point 205° C. (dec.)

IR (Kbr): 1760 cm$^{-1}$ (β-lactam carbonyl)

$^1$H-NMR (200 MHz, DMSO-d$_6$) δ=1.40 (dd, 9H); 3.65 (m, 3H); 4.52 (dd, 1H); 5.63 (s, 2H); 6.28 (t, 1H); 6.80 (s, 1H); 7.80 (s, 2H); 9.25 (s, 1H); 9.30 (d, 1H); 9.80 (s, 1H) ppm.

EXAMPLE 8

[3S-3α(Z),4β]]-3-[[(2-Amino-4-thiazolyl)[[1,1-dimethyl-2-[2-(methylsulfonyl)hydrazino]-2-oxo-ethoxy]imino]acetyl]amino]-4-methyl-2-oxo-1-azetidinesulfonic acid, monopotassium salt

[3S-[3α(Z),4β]]-3-[[(2-Amino-4-thiazolyl)-[(1-carboxy-1-methylethoxy)imino]acetyl]amino]-4-methyl-2-oxo-1-azetidinesulfonic acid (2.18 g), 0.93 g of tributylamine, 0.1 g of N-hydroxybenzotriazole and 0.05 g of dimethylaminopyridine were dissolved in 30 ml of dimethylformamide. A solution of 1.06 g of N,N-dicyclohexylcarbodiimide in 5 ml of dimethylformamide was added, and after 20 minutes stirring at room temperature, a solution of 0.60 g of (methylsulfonyl)hydrazine in 8 ml of dimethylformamide was dropped in. After stirring for 5 hours, the formed dicyclohexylurea was filtered off, the dimethylformamide of the filtrate was distilled off and the residue was dissolved in 20 ml of acetone and filtered. A solution of 1.7 g of potassium perfluorobutanesulfonate in 15 ml of acetone was added. A precipitate of 1.8 g of crude product was obtained and purified by column chromatography on HP-20 using water as eluent and yielding 1.2 g of the title compound, melting point 235° C. (dec).

IR (KBr): 1760 cm$^{-1}$ (β-lactam carbonyl)

$^1$H-NMR (200 MHz, DMSO-d$_6$): δ=1.40 (dd, 9H); 2.90 (s, 3H); 3.66 (m, 1H); 4.5 (dd, 1H); 6.78 (s, 1H); 7.26 (s, 2H); 9.06 (d, 1H); 9.43 (s, broad, 1H); 9.78 (s, broad, 1H); ppm.

EXAMPLE 9

[3S-[3α(Z),4β]]-3-[[[[(2-Phenylhydrazino)-1,1-dimethyl-2-oxoethoxy]imino](2-amino-4-thiazolyl)-acetyl-]amino]-4-methyl-2-oxo-1-azetidinesulfonic acid, monopotassium salt

[3S-[3α(Z),4β]]-3-[[(2-Amino-4-thiazolyl)-[(1-carboxy-1-methylethoxy)imino]acetyl]amino]-4-methyl-2-oxo-1-azetidinesulfonic acid (2.18 g), 0.93 g of tributylamine, 0.1 g of N-hydroxybenzotriazole and 0.05 g of dimethylaminopyridine were dissolved in 30 ml of dimethylformamide and a solution of 1.06 g of N,N-dicyclohexylcarbodiimide was added. After stirring for 20 minutes at room temperature, a solution of 0.54 g of phenylhydrazine in 5 ml of dimethylformamide was dropped in. Stirring for 4 hours, filtering off the formed dicyclohexylurea and distilling off the dimethylformamide of the filtrate yielded a residue which was dissolved in 20 ml of tetrahydrofuran and filtered. To the filtrate was added 1.7 g of potassium perfluorobutanesulfonate and 20 ml of ether yielding 1.8 g of the title compound as a precipitate, melting point 223° C. (dec).

IR (KBr): 1762 cm$^{-1}$ (β-lactam carbonyl)

$^1$H-NMR (200 MHz, DMSO-d$_6$): δ=1.43 (m, 9H); 3.73 (m, 1H); 4.53 (dd, 1H); 6.63 (t, 1H); 6,75 (d, 2H), 6.88 (s, 1H); 7.30 (s, 1H); 7.73 (s, 1H); 9.25 (s, broad, 1H); 9.45 (d, 1H); ppm.

EXAMPLE 10

[3S-[3α(Z), 4β]]-3-[[[[2-[2-(Cyanoacetyl)hydrazino]-1,1-dimethyl-2-oxoethoxy]imino](2-amino-4-thiazolyl)-acetyl]amino]-4-methyl-2-oxo-1-azetidinesulfonic acid, monopotassium salt

[3S-[3α(Z),4β]]-3-[[(2-Amino-4-thiazolyl)-[(1-carboxy-1-methylethoxy)imino]acetyl]amino]-4-methyl-2-oxo-1-azetidinesulfonic acid (2.18 g), 0.93 g of tributylamine, 0.1 g of N-hydroxybenzotriazole and 0.05 g of dimethylaminopyridine were dissolved in 30 ml of dimethylformamide. A solution of 1.06 g of N,N-dicyclohexylcarbodiimide in 5 ml of dimethylformamide was added and after stirring for 20 minutes, a solution of 0.5 g of (cyanoacetyl)hydrazine in 50 ml of dimethylformamide was added. Stirring overnight at room temperature, filtration and distilling off the dimethylformamide of the filtrate yielded an oily residue. It was dissolved in 20 ml of methanol, filtered and to the filtrate a solution of 1.7 g of potassium perfluorobutanesulfonate in 10 ml of acetone was added. Crude product was obtained as a precipitate. Purification by colum chromatography on HP-20 using water as an eluent yielded the title compound, melting point 223° C. (dec).

IR (KBr): 2235 cm$^{-1}$ (cyano); 1765 cm$^{-1}$ (β-lactam carbonyl)

$^1$H-NMR (200 MHz, DMSO-d$_6$): δ=1.41 (m, 9H); 3.70 (m, 1H); 3.73 (s, 2H); 4.51 (dd, 1H); 6.83 (s, 1H); 7.30 (s, 2H); 9.28 (d, 1H); 9.33 (s, broad, 1H); 9.73 (d, broad, AH); 10.30 (s, broad, 1H); ppm.

EXAMPLE 11

[3S-]3α(Z),4β]]-3-[[[[2-[2-(Aminooxyacetyl)-hydrazino]-1,1-dimethyl-2-oxoethoxy]imino](2-amino-4-thiazolyl)acetyl]amino]-4-methyl-2-oxo-1-azetidinesulfonic acid, monopotassium salt

[3S-]3α(Z),4β]]-3-[[(2-Amino-4-thiazolyl)-]1(1-carboxy-1-methylethoxy)imino]acetyl]amino]-4-methyl-2- oxo-1-azetidinesulfonic acid (2.18 g), 0.93 g of tributylamine, 0.1 g of N-hydroxybenzotriazole and 0.05 g of dimethylaminopyridine were stirred at room temperature in 30 ml of dimethylformamide. A solution of 1.06 g of N,N-dicyclohexylcarbodiimide in 5 ml of dimethylformamide was added and, after stirring for 20 minutes, a solution of 0.5 g of (aminooxoacetyl)hydrazine in 20 ml of dimethylformamide was added. Stirring overnight, filtering off the formed dicyclohexylurea and distilling off the dimethylformamide of the filtrate yielded a residue which was dissolved in 30 ml of tetrahydrofuran/methanol (3:1). After filtration, a solution of 1.7 g of potassium perfluorobutanesulfonate in 20 ml of acetone was added. Crude product was obtained as a precipitate. Purification by column chromatography on HP-10 using water as eluent yielded 1.6 g of the title compound, melting point 148° C. (dec).

IR (KBr): 1768 cm$^{-1}$ (β-lactam carbonyl)

$^1$H-NMR (200 MHz DMSO-d$_6$): δ=1.45 (m, 9H); 3.68 (m, 1H); 4.52 (dd, 1H); 6.83 (s, 1H); 7.28 (s, 2H); 8.00 (d, broad, 2H); 9.30 (d, broad, 2H); ppm.

EXAMPLE 12

[3S-[3α(Z),4β]]-3-[[(2-Amino-4-thiazolyl)[[2-hydrazino -1-dimethyl-2-oxoethoxy]imino]acetyl]-amino]-4-methyl-2-oxo-1-azetidinesulfonic acid, and the trifluoroacetate salt thereof Method I (A)

[3S-[3α(Z),4β]]-3-[[(2-Amino-4-thiazolyl)[[2-[2-(triphenylmethyl)hydrazino]-1,1-dimethyl-2-oxoethoxy]imino]acetyl]amino]-4-methyl-2-oxo-1-azetidinesulfonic acid, monopotassium salt

[3S-[3α(Z),4β]]-3-[[(2-Amino-4-thiazolyl)-[(1-carboxy-1-methylethoxy)imino]acetyl]amino]-4-methyl-2-oxo-1-azetidinesulfonic acid (2.18 g), 0.1 g of N-hydroxybenzotriazole, 0.05 g of dimethylaminopyridine and 0.93 g of tributylamine were dissolved in 20 ml of dimethylformamide. With stirring, a solution of 1.1 g of N,N-dicyclohexylcarbodiimide in 10 ml of dimethylformamide was added. After stirring at room temperature for 15 minutes, a solution of 1.55 g of (tripheylmethyl)hydrazine, hydrochloride and 0.93 g of tributylamine in 20 ml of dimethylformamide were added. Stirring overnight, filtering off the formed dicyclohexylurea and distilling off the dimethylformamide of the filtrate yielded a residue which was dissolved in 20 ml of acetone and filtered. To the filtrate was added 150 ml of ether and a solution of 3.40 g of potassium perfluorobutanesulfonate in 30 ml of aceonte. Crude product was obtained as a precipitate (2.2 g). Purification by column chromatography on HP-20 using water and water/tetrahydrofuran (9:1) as eluents yielded the title compound, melting point 182°–184° C. (dec).

IR (KBr): 1760 cm$^{-1}$ (β-lactam carbonyl)

$^1$H-NMR (200 MHz, DMSO-d$_6$): δ=1.10 (d, 6H); 1.38 (d, 3H); 3.63 (m, 1H); 4.38 (dd, 1H); 5.78 (d, 1H); 6.58 (s, 1H); 7.33 (m, 17H); 8.00 (d, 1H); 9.25 (d, 1H); ppm.

(B)

[3S-[3α(Z),4β]]-3-[[(2-Amino-4-thiazolyl)[[2-hydrazino-1, 1-dimethyl-2-oxoethoxy]imino]acetyl]-amino]-4-methyl-2-oxo-1-azetidinesulfonic acid

[3S-[3α(Z),4β]]-3-[[(2-Amino-4-thiazolyl)[[2-[2-(triphenylmethyl)hydrazino]-1,1-dimethyl-2-oxo-ethoxy]imino]acetyl]amino]-4-methyl -2-oxo-1-azetidinesulfonic acid, monopotassium salt (0.8 g) was suspended in 20 ml of dichloromethane. At 0° C., with stirring, 10 ml of formic acid (98%) was added. After continuous stirring for 20 minutes, the clear solution was transferred into 100 ml of ether. A precipitate of the formic acid salt of the title compound and potassium formiate were obtained. The precipitate was stirred in 30 ml of acetonitrile and 5 ml of N-Methyl-N-(trimethylsilyl)trifluoroacetamide was added. Stirring for 10 minutes, filtration and the addition of 5 ml of methanol to the filtrate yielded the title compound as a crystalline precipitate.

IR (KBr): 1762 cm$^{-1}$ (β-lactam carbonyl)

$^1$H-NMR (200 MHz, DMSO-d$_6$): δ=1.38 (m, 9H); 3.68 (m, 1H); 4.5 (dd, 1H); 6.80 (s, 1H); 7.30 (m, broad, 4H); 9.15 (s, broad, 1H); 9.38 (d, broad, 1H); ppm.

Method II

[3S-[3α(Z),4β]]-3-[[(2-Amino-4-thiazolyl)[[2-hydrazino -1,1-dimethyl-2-oxoethoxy]imino]acetyl]-amino]-4-methyl-2-oxo-1-azetidinesulfonic acid, trifluoroacetate salt (1:2)

[3S-[3α(Z),4β]]-3-[[(2-Amino-4-thiazolyl)-[[1, 1-dimethylethoxy)carbonyl]hydrazino]-2-oxo-1-azetidinesulfonic acid, monopotassium salt (10 g) was dissolved in 30 ml of dichloromethane and added dropwise to 60 ml of trifluoroacetic acid with stirring at −10° C. After 20 minutes of stirring, the reaction was complete. The addition of 200 ml of ether to the solution precipitated 7.8 g of the title compound, melting point 220° C., (dec).

EXAMPLE 13

[3S-3α(Z),4β]]-3-[[(2-Amino-4-thiazolyl)[[1, 1-dimethyl-2-[2-(2-pyriidinyl)hydrazino]-2-oxoethoxy]-imino]acetyl]amino]-4-methyl-2-oxo-1-azetidinesulfonic acid, monopotassium salt

[3S-[3α(Z),4β]]-3-[[(2-Amino-4-thiazolyl)-]1(1-carboxy-1-methylethoxy)imino]acetyl]amino]-4-methyl-2-oxo-1-azetidinesulfonic acid (1.04 g) 0.05 g of N-hydroxybenzotriazole, 0.025 g of dimethylaminopyridine and 0.88 g of trioctylamine were dissolved in 20 ml of dimethylformamide. N,N-Dicyclohexylcarbodiimide (0.55 g) in 10 ml of tetrahydrofuran was added. Stirring for 15 minutes at room temperature, followed by the addition of 0.3 g of (2-pyridinyl)hydrazine in 5 ml of dimethylformamide and overnight stirring completed the reaction. Dicyclohexylurea was filtered off, the solvents of the filtrate were distilled off and the residue was dissolved in 20 ml of tetrahydrofuran and filtered. Potassium perfluorobutanesulfonate (0.85 g) was added, stirring for 5 minutes followed by the addition of 10 ml of ether formed crude product as a precipitate (0.9 g). Purification by column chromatography on HP-20 yielded the title compound, melting point 205°–207° C. (dec).

IR (KBr): 1762 cm$^{-1}$ (β-lactam carbonyl)

$^1$H-NMR (200 MHz, DMSO-d$_6$): δ=1.40 (dd, 9H); 3.65 (m, 1H); 4.53 (dd, 1H); 6.65 (m, 2H); 6.84 (s, 1H); 7.30 (s, 2H); 7.43 (t, 1H); 8.00 (d, 1H); 8.18 (s, 1H); 9.35 (s, 1H); 9.40 (d, 1H); ppm.

EXAMPLE 14

[3S-[3α(Z),4β]]-3-[[[[2-[2-(3-Pyridinylcarbonyl)-hydrazino]-1,
1-dimethyl-2-oxoethoxy]imino](2-amino-4-thiazolyl)acetyl]amino]-4-methyl-2-oxo-1-azetidinesulfonic acid, monopotassium salt

[3S-[3α(Z),4β]]-3-[[(2-Amino-4-thiazolyl)-[(1-carboxy-1-methylethoxy)imino]acetyl]amino]-4-methyl-2-oxo-1-azetidinesulfonic acid (2.18 g), 0.93 g of tributylamine, 0.1 g of N-hydroxybenzotriazole and 0.05 g of dimethylaminopyridine in 30 ml of dimethylformamide were stirred and a solution of 1.06 g of N,N-dicyclohexylcarbodiimide in 10 ml of dimethylformamide was dropped in. After 30 minutes, a solution of 0.68 g of (3-pyridinylcarbonyl)hydrazine in 10 ml of dimethylformamide was added. Stirring overnight, filtering off the dicyclohexylurea, and stripping off the dimethylformamide of the filtrate yielded a residue which was dissolved in 30 ml of acetone. After adding 1.7 g of potassium perfluorobutanesulfonate in 20 ml of acetone, the title compound was obtained as a precipitate (1.8 g), melting point 243° C. (dec).

IR (KBr): 1760 cm$^{-1}$ (β-lactam carbonyl)
$^1$H-NMR (200 MHz, DMSO-d$_6$): δ=1.44 (dd, 9H); 3.70 (m, 1H); 4.53 (dd, 1H); 6.85 (s, 1H); 7.28 (s, 2H); 7.51 (m, 1H); 8.20 (m, 1H); 8.73 (q, 1H); 9.01 (d, 1H); 9.30 (d, 1H); 9.50 (s, 1H); 10.63 (s, broad, 1H); ppm.

EXAMPLE 15

[3S-[3α(Z),4β]]-3-[[(2-Amino-4-thiazolyl)[[2-[2-(aminocarbonyl)-2-methylhydrazino]-1,
1-dimethyl-2-oxoethoxy]imino]acetyl]amino]-4-methyl-2-oxo-1-azetidinesulfonic acid, monopotassium salt

[3s-[3α(Z),4β]]-3-[[(2-Amino-4-thiazolyl)-[(1-carboxy-1-methylethoxy)imino]acetyl]amino]-4-methyl-2-oxo-1-azetidinesulfonic acid (1.09 g), 0.47 g of tributylamine, 0.05 g of N-hydroxybenzotriazole and 0.025 g of dimethylaminopyridine were dissolved in 15 ml of dimethylformamide. After adding a solution of 0.55 g of N,N-dicyclohexylcarbodiimide in 5 ml of dimethylformamide and stirring at room temperature for 15 minutes, a solution of 0.4 g of 2-(aminocarbonyl)-2-methyl-hydrazine and 0.47 g of tributylamine in 10 ml of tetrahydrofuran was added. Overnight stirring, filtering off the dicyclohexylurea and distilling off the solvents of the filtrate yielded a residue which was dissolved in 20 ml of tetrahydrofuran and filtered. To the filtrate was added a solution of 0.85 g of potassium perfluorobutanesulfonate in 20 ml of tetrahydrofuran and 50 ml of ether. Crude product (1.1 g) was obtained as a precipitate. Purification by column chromatography on HP-20 yielded the title compound, melting point 203°–205° C. (dec).

IR (KBr): 1762 cm$^{-1}$ (β-lactam carbonyl)
$^1$H-NMR (200 MHz, DMSO-d$_6$): δ=1.36 (s, 6H); 1.40 (d, 3H); 2.93 (s, 3H); 3.65 (m, 1H); 4.53 (dd, 1H); 6.08 (s, broad, 2H); 6.78 (s, 1H); 7.23 (s, 2H); 9.25 (d, 1H); 0.78 (s, 1H); ppm.

EXAMPLE 16

[3S-[3α(Z),4β]]-3-[[(2-Amino-4-thiazolyl)[[2-[2-[(methylamino)carbonyl]hydrazino]-1,
1-dimethyl-2-oxoethoxy]imino]acetyl]amino]-4-methyl-2-oxo-1-azetidinesulfonic acid, monopotassium salt

[3S-3[α(Z),4β]]-3-[[(2-Amino-4-thiazolyl)-[(1-carboxy-1-methylethoxy)imino]acetyl]amino]-4-methyl-2-oxo-1-azetidinesulfonic acid (1.09 g), 0.47 g of tributylamine, 0.05 g of N-hydroxybenzotriazole and 0.025 g of dimethylaminopyridine were dissolved in 20 ml of dimethylformamide. N,N-Dicyclohexylcarbodiimide (0.55 g) was added, and after 20 minutes stirring at room temperature a solution of 0.28 g of [(methylamino)carbonyl]-hydrazine, hydrochloride and 0.4 g of tributylamine in 20 ml of dimethylformamide was also added. Overnight stirring, filtering off the dicyclohexylurea and distilling off the dimethylformamide of the filtrate yielded a residue, which was dissolved in 30 ml of dimethylformamide and filtered. To the filtrate was added a solution of 1.7 g of potassium perfluorobutanesulfonate in 20 ml of acetone. Crude product (1.1 g) was obtained as a precipitate. Purification by column chromatography on HP-20 using water as an eluent yielded the title compound, melting point 218° C. (dec).

IR (KBr): 1760 cm$^{-1}$ (β-lactam carbonyl)
$^1$H-NMR (200 MHz, DMSO-d$_6$): δ=1.36 (d, 6H); 1.39 (d, 3H); 2.51 (d, 2H); 3.66 (m, 1H); 4.52 (dd, 1H); 5.65 (d, broad, 1H); 6.80 (s, 1H); 7.28 (s, 2H); 7.86 (s, 1H); 9.23 (s, 1H); 9.33 (d, 1H); ppm.

EXAMPLE 17

[3S-[3α(Z),4β]]-3-[[(2-Amino-4-thiazolyl)[[2-[2-[methylamino)thioxomethyl]hydrazino]-1,
1-dimethyl-2-oxoethoxy]imino]acetyl]amino]-4-methyl-2-oxo-1-azetidinesulfonic acid, monopotassium salt

[3S-[3α(Z),4β]]-3-[[(2-Amino-4-thiazolyl)-[(1-carboxy-1-methylethoxy)imino]acetyl]amino]-4-methyl-2-oxo-1-azetidinesulfonic acid (1.09 g), 0.05 g of N-hydroxybenzotriazole, 0.025 g of dimethylaminopyridine and 0.88 g of trioctylamine were dissolved in 50 ml of of tetrahydrofuran and 0.55 g of N,N-dicyclohexylcarbodiimide was added. After stirring for 30 minutes at room temperature, 0.27 g of [(methylamino)thioxomethyl]hydrazine in 20 ml of tetrahydrofuran was added. Overnight stirring, filtering off the formed dicyclohexylurea and adding 0.85 g of potassium perfluorobutanesulfonate in 15 ml of acetone to the filtrate formed crude product as a precipitate. Adding ether yielded a second crop. (Total 1.1 g). Purification by column chromatography on HP-20 using water as an eluent yielded the title compound, melting point 206°–208° C., (dec).

IR (KBr): 1760 cm$^{-1}$ (β-lactam carbonyl)
$^1$H-NMR (200 MHz, DMSO-d$_6$): δ=1.38 (d, 6H); 1.40 (d, 3H); 2.85 (d, 3H); 3.68 (m, 1H); 4.52 (dd, 1H); 6.79 (d, broad, 1H); 6.89 (s, 1H); 7.33 (s, 2H); 9.28 (d, 1H); 9.46 (s, broad, 1H); 9.53 (s, broad, 1H); ppm.

EXAMPLE 18

[3S-[3α(Z),4β]]-3-[[(2-Amino-4-thiazolyl)[[2-[2-[imino(-methylthio)methyl]hydrazino]-1,
1-dimethyl-2-oxoethoxy]imino]acetyl]amino]-4-methyl-2-oxo-1-azetidinesulfonic acid, monopotassium salt

[3S-[3α(Z),4β]]-3-[[(2-Amino-4-thiazolyl)-[(1-carboxy-1-methylethoxy)imino]acetyl]amino]-4-methyl-2-oxo-1-azetidinesulfonic acid (2.18 g), 0.93 g of tributylamine, 0.1 g of N-hydroxybenzotriazole and 0.05 g of dimethylaminopyridine were dissolved in 30 ml of dimethylformamide. N,N-Dicyclohexylcarbodiimide (1.06 g) in 5 ml of dimethylformamide was added and, after stirring for 20 minutes, a solution of 1.17 g of [imino(methylthio)methyl]hydrazine, hydrogen iodide salt and 0.93 g of tributylamine in 15 ml of dimethylformamide was also added. Continuous stirring overnight at 5° C., filtering off the dicyclohexylurea and distilling off the dimethylformamide of the filtrate yielded an oily residue. The residue was dissolved in 30 ml of tetrahydrofuran and 5 ml of methanol, filtered and a solution of 3.4 g of potassium perfluorobutanesulfonate in 20 ml of acetone was added. Crude product (1.2 g) was obtained as a precipitate. Purification by column chromatography on HP-20 using water as an eluent yielded 1.4 g of the title compound, melting point 208° C., (dec).

IR (KBr): 1765 cm$^{-1}$ ($\beta$-lactam carbonyl)

$^1$H-NMR (200 MHz, DMSO-d$_6$): $\delta$=1.36 (d, 6H); 1.40 (d, 3H); 2.28 (s, 3H); 3.68 (m, 1H); 4.51 (dd, 1H); 6.38 (s, broad, 2H); 6.81 (s, 1H); 7.28 (s, 2H); 9.06 (s, broad, 1H); 9.40 (d, broad, 1H); ppm.

EXAMPLE 19

[3S-[3$\alpha$(Z),4$\beta$]]-3-[[(2-Amino-4-thiazolyl)[[2-[2-[aminothioxomethyl)hydrazino]-1,1-dimethyl-2-oxoethoxy]imino]acetyl]amino-4-methyl-2-oxo-1-azetidinesulfonic acid, monopotassium salt

[3S-[3$\alpha$(Z),4$\beta$]]-3-[[(2-Amino-4-thiazolyl)-[(1-carboxy-1-methylethoxy)imino]acetyl]amino]-4-methyl-2-oxo-1-azetidinesulfonic acid (0.66 g), 0.3 g of tributylamine, 0.26 g of N-hydroxybenzotriazole and 0.01 g of dimethylaminopyridine were dissolved in 10 ml of dimethylformamide and a solution of 0.33 g of N,N-dicyclohexylcarbodiimide in 5 ml of dimethylformamide was added. After stirring for 20 minutes at room temperature, a solution of 0.28 g of (aminothioxomethyl)hydrazine in 10 ml of dimethylformamide was also added. Stirring was continued for 24 hours, formed dicyclohexylurea was filtered off and the dimethylformamide of the filtrate was distilled off. The residue was dissolved in 20 ml tetrahydrofuran/methanol (1.1), filtered and a solution of 0.51 g of potassium perfluorobutanesulfonate in 5 ml of methanol was added followed by 20 ml of ether. The resultant precipitate of crude product was purified by column chromatography on HP-20 using water as an eluent and yielding 0.8 g of the title compound, melting point 218° C., (dec).

IR (KBr): 1768 cm$^{-1}$ ($\beta$-lactam carbonyl)

$^1$H-NMR (200 MHz, DMSO-d$_6$) $\delta$=1.23 (d, 3H); 1.35 (d, 6H); 4.05 (m, 1H); 5.10 (m, 1H); 6.80 (s, 1H); 6.93 (s, broad, 1H, CSNH$_2$); 7.33 (s, broad, 2H); 8.10 (s, broad, 1H, CSNH$_2$), 9.14 (d, broad, 1H); 9.40 (s, broad, 1H); 9.65 (s, broad, 1H); ppm.

EXAMPLE 20

[3S-[3$\alpha$(Z),4$\beta$]]-3-[[(2-Amino-4-thiazolyl)[[2-[2-[3,4-bis(acetyloxy)benzoyl]hydrazino]-1,1-dimethyl-2-oxoethoxy]imino]acetyl]amino]-4-methyl-2-oxo-1-azetidinesulfonic acid, monopotassium salt

[3S-[3$\alpha$(Z),4$\beta$]]-3-[[(2-Amino-4-thiazolyl)-[[2-hydrazino-1,1-dimethyl-2-oxoethoxy]imino]acetyl]amino]-4-methyl-2-oxo-1-azetidinesulfonic acid, trifluoroacetate salt (1:2) (1.36 g) and 1.47 g of tributylamine were dissolved in 15 ml of dimethylformamide. At 0° C., with stirring, a solution of 0.75 g of 3,4-(diacetyloxy)benzoyl chloride in 5 ml of dimethylformamide was dropped in. After stirring for 3 hours, the dimethylformamide was distilled off and the residue was dissolved in 20 ml of tetrahydrofuran and filtered. To the filtrate was added 2.75 g of potassium perfluorobutanesulfonate. After stirring for 10 minutes, 20 ml of ether was added and crude product was obtained as a precipitate. This was purified by liquid chromatography on XAD-2* using water and water/tetrahydrofuran (9.5:0.5) as eluents, yielding 1.1 g of the title compound, melting point 221° C. (dec).

*XAD-2: macroreticular styrene-divinylbenzene copolymer, Rohm and Haas Company

IR (KBr): 1765 cm$^{-1}$ ($\beta$-lactam carbonyl)

$^1$H-NMR (200 MHz, DMSO-d$_6$) $\delta$=1.41 (d, 3H); 1.48 (d, 6H); 2.29 (s, 6H); 3.70 (m, 1H); 4.06 (dd, 1H); 6.85 (s, 1H); 7.26 (s, 2H); 7.40 (d, 1H); 7.81 (m, 2H); 9.30 (d, 1H); 9.48 (s, 1H); 10.49 (s, 1H); ppm.

EXAMPLE 21

[3S-[3$\alpha$(Z),4$\beta$]]-3-[[(2-Amino-4-thiazolyl)[[1,1-dimethyl-2-[2-[(2-amino-4-thiazolyl)acetyl]-hydrazino]-2-oxoethoxy]imino]acetyl]amino]-4-methyl-2-oxo-1-azetidinesulfonic acid, monopotassium salt

[3S-[3$\alpha$(Z),4$\beta$]]-3-[[(2-Amino-4-thiazolyl)-](1-carboxy-1-methylethoxy)imino]acetyl]amino]-4-methyl-2-oxo-1-azetidinesulfonic acid (1.09 g), 0.47 g of tributylamine, 0.1 g of N-hydroxybenzotriazole and 0.05 g of dimethylaminopyridine were dissolved in 10 ml of dimethylformamide and 0.54 g of N,N-dicyclohexylcarbodiimide was added. After stirring for 20 minutes at room temperature, 0.45 g of [(2-amino-4-thiazolyl)acetyl]hydrazine was added. Overnight stirring, filtration from the formed dicyclohexylurea and distilling of the dimethylformamide of the filtrate yielded a residue. It was dissolved in 10 ml of tetrahydrofuran, filtered again and 1.7 g of potassium perfluorobutanesulfonate and 10 ml of ether were added to the filtrate yielding a precipitate. The crude product was purified by column chromatography on HP-20 using water as an eluent, yielding 0.67 g of the title compound, melting point 147° C. (dec).

IR (KBr): 1765 cm$^{-1}$ ($\beta$-lactam carbonyl)

$^1$H-NMR (200 MHz, DMSO-d$_6$) $\delta$=1.43 (2d, 9H); 3.30 (d, 2H); 3.71 (m, 1H); 4.51 (dd, 1H); 6.31 (s, 1H); 6.80 (s, 1H); 6.82 (s, 2H); 7.62 (s, 2H); 9.28 (s, broad, 3H); 9.77 (s, broad, 1H); ppm.

EXAMPLE 22

[3S-[3$\alpha$(Z),4$\beta$]]-3-[[(2-Amino-4-thiazolyl)[[2-[2-[(2,3-dihydroxyphenyl)methylene]hydrazino]-1,1-dimethyl-2-oxoethoxy]imino]acetyl]amino]-4-methyl-2-oxo-1-azetidinesulfonic acid, monopotassium salt, dimethylformamide (1:2)

[3S-[3$\alpha$(Z),4$\beta$]]-3-[[(2-Amino-4-thiazolyl)-[[2-hydrazino-1,1-dimethyl-2-oxoethoxy]imino]acetyl]amino]-4-methyl-2-oxo-1-azetidinesulfonic acid, trifluoroacetate salt (1:2) (0.68 g) and 0.37 g of tributylamine were dissolved in 10 ml of dimethylformamide. A solution of 0.14 g of 2,3-dihydroxybenzaldehyde in 10 ml of dimethylformamide was added. After stirring for 12 hours, the solution was filtered and the dimethylformamide filtrate was distilled off. The residue was dissolved in 30 ml of methanol and a solution of 1.1 g of potassium perfluorobutanesulfonate in 20 ml of methanol was added. The title compound (0.45 g) was obtained as a crystalline precipitate, melting point 199° C. (dec).

IR (KBr): 1770 cm$^{-1}$ ($\beta$-lactam carbonyl)

$^1$H-NMR (200 MHz, DMSO-d$_6$) $\delta$: 1.42 (d, 3H); 1.50 (d, 6H); 3.80 (m, 1H); 4.50 (m, 1H); 4.68 (s, broad, 2H); 6.65–7.00 (m, 4H); 7.25 (s, broad, 2H); 4.49 (s, 1H); 9.43 (d, 2H); 10.99 (s, 1H); ppm.

EXAMPLE 23

[3S-[3α(Z),4β]]-3-[[(2-Amino-4-thiazolyl)[[2-[2-[(3,4-dihydroxyphenyl)methylene]hydrazino]-1,1-dimethyl-2-oxoethoxy]imino]acetyl]amino]-4-methyl-2-oxo-1-azetidinesulfonic acid, monopotassium salt

[3S-[3α(Z),4β]]-3-[[(2-Amino-4-thiazolyl)-[[2-hydrazino-1,1-dimethyl-2-oxoethoxy]imino]acetyl]amino]-4-methyl-2-oxo-1-azetidinesulfonic acid, trifluoroacetate salt (1:2) (0.68 g) and 0.37 g of tributylamine were dissolved in 15 ml of dimethylformamide. To this solution was added 1 g of molecular sieves (3 angstroms) together with 0.14 g of 3,4-dihydroxybenzaldehyde. After stirring for 8 hours at room temperature, the solution was filtered and the filtrate was distilled off. The residue was dissolved in methanol and filtered again. To the filtrate was added 1.1 g of potassium perfluorobutanesulfonate and 10 ml of diethyl ether. Crude product was obtained as a precipitate. Purification by liquid chromatography on XAD-2 using water and water/methanol (9.7:0.3) as eluents yielded 0.8 g of the title compound, melting point 258° C. (dec.).

IR (KBr): 1768 cm$^{-1}$ (β-lactam carbonyl)

$^1$H-NMR (200 MHz, DMSO-d$_6$) δ: 1.41 (d, 3H); 1.46 (s, 6H); 3.38 (s, broad, 2H); 3.78 (m, 1H); 4.51 (dd, 1H); 6.75 (m, 1H); 6.83 (s, 1H); 6.90 (m, 1H); 7.25 (s, broad, 2H); 8.13 (s, 1H); 9.45 (s, broad, 1H); 10.40 (s, broad, 1H); ppm.

EXAMPLE 24

(Z)-2-Amino-α-[[1,1-dimethyl-2-[2-[(1,1-dimethylethoxy)-carbonyl]hydrazino]-2-oxoethoxy]imino]-4-thiazoleacetic acid (A)
1-[2-[(1,3-Dihydro-1,3-dioxo-2H-isoindol-2-yl)oxy]-2-methyl-1-oxopropyl]-2-[(1,1-dimethylethoxy)-carbonyl]

2-[(1,3-Dihydro-1,3-dioxo-2H-isoindol-2-yl)-oxy]-2-methylpropanoyl chloride (34.5 g) was dissolved in 200 ml of dichloromethane. At 0° C., with stirring, a solution of 17 g of [(1,1-dimethylethoxy)carbonyl]hydrazine and 13 g of triethylamine in 80 ml of dichloromethane was added. After stirring overnight, 300 ml of ice water was added, and after stirring for 5 minutes, the organic phase was separated and extracted with 100 ml of 5% sodium bicarbonate solution and then with 100 ml of water. After drying over sodium sulfate, the dichloromethane was evaporated. The oily residue crystallized after several hours, yielding 42.2 g of white crystals.

IR (KBr): 1800 cm$^{-1}$ (carbonyl phthalimido); 1740 cm$^{-1}$ (carbonyl ester).

$^1$H-NMR (90 MHz, DMSO-d$_6$): δ=1.34 (s, 9H); 1.50 (s, 6H); 7.93 (s, 4H); 8.81 (s, broad, 1H); 9.69 (s, 1H); ppm.

(B)
1-[2-(Aminooxy)-2-methyl-1-oxopropyl]-2-[(t-butyloxy)carbonyl]hydrazide

1-[2-[(1,3-Dihydro-1,3-dioxo-2H-isoindol-2-yl)oxy]-2-methyl-1-oxopropyl]-2-[(1,1-dimethylethoxy)carbonyl](18.2 g) was dissolved in 200 ml of dichloromethane and at 0° C. a solution of 2.3 g of N-methylhydrazine was added dropwise in 300 ml of dichloromethane. After 4 hours stirring, the reaction mixture was filtered and the dichloromethane of the filtrate was evaporated yielding an oily residue of the title compound (24.2 g), which crystallized after standing im the cold.

$^1$H-NMR (90 MHz, DMSO-d$_6$): δ=1.30 (s, 9H); 1.46 (s, 6H); 5.95 (s, broad, 2H); 8.59 (s, broad, 1H); 9.35 (s, broad, 1H); ppm.

(Z)-2-Amino-α-[[1,1-dimethyl-2-[2-[(1,1-dimethylethoxy)carbonyl]-hydrazino]-2-oxoethoxy]imino]-4-thiazoleacetic acid.

(Z)-2-Amino-4-thiazoleglyoxylic acid (1.72 g) was suspended in 30 ml of water/tetrahydrofuran (1:1) and 2.33 g of 1-[2-(aminooxy)-2-methyl-1-oxopropyl]-2-[(t-butyloxy)carbonyl]hydrazine was added; the pH was adjusted to 5.6 with sodium bicarbonate. Stirring overnight formed a clear solution. The dimethylformamide was evaporated and the water solution was adjusted to pH 2 with 2 N phosphoric acid at 5° C. Crude product was obtained as an oily precipitate which crystallized after treatment with ether. Recrystallization from dimethylformamide/isopropanol yielded 3.2 g of white crystals, melting point 195° C. (dec).

IR (KBr): 1730 cm$^{-1}$ $^1$H-NMR (90 MHz, DMSO-d$_6$) δ=1.41 (d +s, 15H); 6.92 (s, 1H); 7.27 (s, broad, 2H); 8.00 (s, broad, 1H); 8.71 (s, broad, 1H); 9.15 (s, broad, 1H).

EXAMPLE 25

[3S-[3α(Z),4β]]-3-[[(2-Amino-4-thiazolyl)[[2-(2,2-dimethylhydrazino)-1,1-dimethyl-2-oxo-ethoxy]imino]acetyl]amino]-4-methyl-2-oxo-1-azetidinesulfonic acid, monopotassium salt

[3S-[3α(Z),4β]]-3-[[(2-Amino-4-thiazolyl)-[(1-carboxy-1-methylethoxy)imino]acetyl]amino]-4-methyl-2-oxo-1-azetidinesulfonic acid (1.09 g), 0.47 g of tributylamine, 0.05 g of N-hydroxybenzotriazole and 0.005 g of 4-dimethylaminopyridine were dissolved in 10 ml of dimethylformamide. With stirring, 0.6 g of dicyclohexylcarbodiimide was added in 5 ml of dimethylformamide. After 20 minutes stirring at room temperature, a solution of 0.15 g of 1,1-dimethylhydrazine in 5 ml of dimethylformamide was added. Stirring overnight, filtering off the formed dicyclohexylurea and distilling off the dimethylformamide of the filtrate yielded an oily residue. It was dissolved in 25 ml of acetone and 0.85 g of potassium perfluorobutanesulfonate was added. Crude product was obtained as a precipitate and purified by column chromatography on HP-20 using water as an eluent. The product had a melting point of 242° C. (dec).

EXAMPLE 26

[3S-[3α(Z),4β]]-3-[[2-Amino-4-thiazolyl)[[2-[2-(1-pyradinylacetyl)hydrazino]-1,1-dimethyl-2-oxoethoxy]imino]acetyl]amino]-4-methyl-2-oxo-1-azetidinesulfonic acid, inner salt

[3S-[3α(Z),4β]]-3-[[(2-Amino-4-thiazolyl)-](1-carboxy-1-methylethoxy)imino]acetyl]amino]-4-methyl-2-oxo-1-azetidinesulfonic acid (2.18 g), 0.93 g of tributylamine, 0.1 g of N-hydroxybenzotriazole and 0.05 g of 4-dimethylaminopyridine were dissolved in 20 ml of dimethylformamide and a solution of 1.06 g of dicyclohexylcarbodiimide in 5 ml of dimethylformamide was added. After stirring for 15 minutes at room temperature, a solution of 0.94 g Girard Reagent P in 20 ml of dimethylformamide was added. After 3 hours of stirring, formed dicyclohexylurea was filtered off and the dimethylformamide of the filtrate was distilled off. Addition of 50 ml of tetrahydrofuran to the residue yielded 1.8 g of crude product, which was purified by column chromatography on HP-20 using water as an eluent, yielding 0.63 g of product, melting point 235° C.

EXAMPLE 27

[3S-3α(Z),4β]]-3-[[(2-Amino-4-thizolyl)][2-[2-[3,4-bis(-hydroxy)benzoyl]hydrazino]-1,1-dimethyl-2-oxoethoxy]imino]acetyl]amino]-4-methyl-2-oxo-1-azetidinesulfonic acid, monopotassium salt

(A)
1-[3,4-bis(Acetyloxy)benzoyl]-2-[(t-butyloxy)-carbonyl]hydrazine

[(t-Butyuloxy)carbonyl]hydrazine (1.32 g) and 1.01 g of triethylamine were dissolved in 15 ml of dichloromethane. At 0° C., 2.5 g of 3,4-(diacetyloxy)benzoyl chloride dissolved in 10 ml of dichloromethane was dropped in with stirring. After 2 hours, the dichloromethane was twice extracted with ice water (50 ml portions). The organic layer was dried over sodium sulfate and the solvent evaporated, yielding 2.9 g of the title compound as a white crystalline material, melting point 78°–82° C.

(B)
1-[3,4-bis(Hydroxy)benzoyl]-2-[(t-butyloxy)-carbonyl]hydrazine

1-[3,4-bis(Acetyloxy)benzoyl]-2-[(t-butyloxy)carbonyl]hydrazine (2.6 g) was dissolved in 50 ml of methanol and 5 ml of water. At 0° C., ammonia (gas) was bubbled into the solution for 10 minutes. After standing overnight in a refrigerator, the solution was evaporated, and to the remaining oil, 10 ml of dichloromethane was added. This yielded 1.5 g of the title compound, melting point 148° C.

(C) [3,4-bis(Acetyloxy)benzoyl]hydrazine, trifluoroacetate salt

1-[3,4-bis(Hydroxy)benzoyl]-2-[(t-butyloxy)-carbonyl]hydrazine (1.4 g) was stirred in 10 ml of trifluoroacetic acid for 30 minutes at 5° C. The title compound was obtained as a precipitate, which was isolated and washed three times with 10 ml of portions of diethyl ester (anhydrous); melting point 173° C.

(D)
[3S-[3α(Z),4β]]-3-[[(2-Amino-4-thiazolyl)][2-[2-[3,4-bis(hydroxy)benzoyl]hydrazino]-1,1-dimethyl-2-oxoethoxy]imino]acetyl]amino]-4-methyl-2-oxo-1-azetidinesulfonic acid, monopotassium salt

[3,4-bis(Acetyloxy)benzoyl]hydrazine, trifluoroacetate salt was coupled with [3S-3α(Z), 4β]]-3-[[(2-amino-4-thiazolyl)[(1-carboxy-1-methylethoxy)imino]acetyl]amino]-4-methyl-2-oxo-1-azetidinesulfonic acid using tributylamine, N-hydroxybenzotriazole, dimethylaminopyridine, dicyclohexylcarbodiimide, and potassium perfluorobutanesulfonate, using the procedure described in previous examples, yielding the title compound, melting point 247° C. (dec).

$^1$H-NMR (200 MHz, DMSO-d$_6$) δ=1.38 (d, 3H); 1.42 (d, 6H); 3.35 (s, broad, 2H (HO-)); 3.69 (m, 1H); 4.05 (dd, 1H); 6.75 (d, 1H); 7.25 (m, 3H); 9.32 (d+s, 2H); 10.01 (s, broad, 1H); ppm.

IR(KBr): 1780 cm$^{-1}$ (β-lactam carbonyl).

EXAMPLE 28

[3S-3α(Z),4β]]-3-[[(2-Amino-4-thiazolyl)][2-[2-[3,4-bis(hydroxy)benzoyl]hydrazino]-1,1-dimethyl-2oxoethoxy]imino]acetyl]amino]-4-[[(aminocarbonyl)methyl]thio]-2-oxo-1-azetidinesulfonic acid, monopotassium salt Following the procedure of example 27, but substituting [3S-[3α(Z),4β]]-3-[[(2-amino-4-thiazolyl)[(1-carboxy-1-methylethoxy)imino]-acetyl]amino]-4-[[(aminocarbonyl)methyl]thio-2-oxo-1-azetidinesulfonic acid for [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid, yielded the title compound.

Additional compounds falling within the scope of this invention are set forth below.

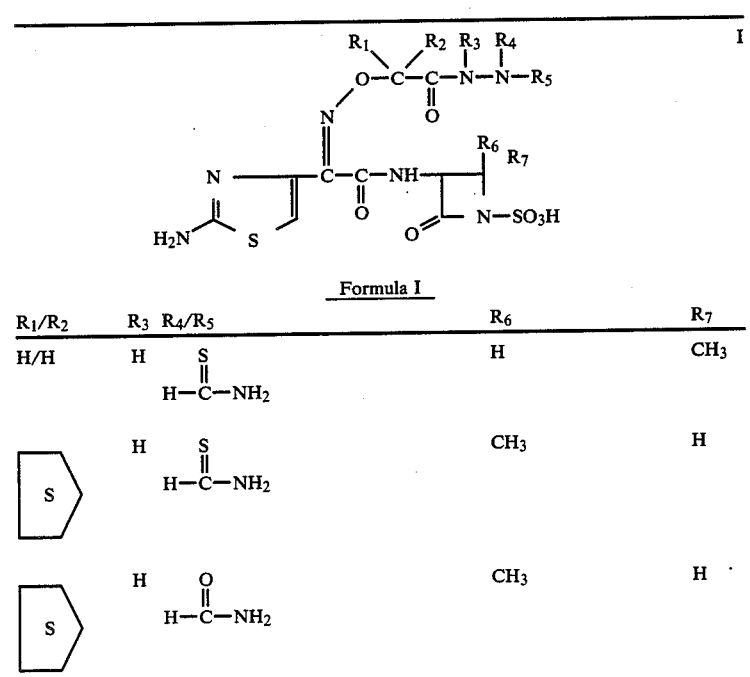

Formula I

| R$_1$/R$_2$ | R$_3$ | R$_4$/R$_5$ | R$_6$ | R$_7$ |
|---|---|---|---|---|
| H/H | H | H—C(=S)—NH$_2$ | H | CH$_3$ |
| [S-thiophene] | H | H—C(=S)—NH$_2$ | CH$_3$ | H |
| [S-thiophene] | H | H—C(=O)—NH$_2$ | CH$_3$ | H |

-continued $$\underset{\text{Formula I}}{\text{structure I}}$$

Structure I: guanidino-thiazole-vinyl group with C=N-O-C(R1)(R2)-C(=O)-N(R3)-N(R4)(R5), and -C(=O)-NH-C(R6)(R7)-C(=O)-N(SO₃H)- moiety.

| R₁/R₂ | R₃ | R₄/R₅ | R₆ | R₇ |
|---|---|---|---|---|
| —(CH₂)₄— (cyclopentyl, S) | H | H-C(=O)-NH₂ | H | CH₃ |
| CH₃/H | H | H-C(=O)-C(=O)-OH | H | CH₃ |
| CH₃/H | H | H-C(=S)-NH-NH₂ | H | CH₃ |
| CH₃/CH₃ | H | H-C(=O)-NH-C(=O)-NH₂ | H | CH₃ |
| CH₃/CH₃ | H | H-C(=O)-NH₂ | -S-CH₂-C(=O)-NH₂ | H |
| CH₃/CH₃ | H | H-C(=O)-NH-CH₂-C(=O)-OH | H | CH₃ |
| CH₃/CH₃ | H | H-C(=O)-CH₂-C(=O)-NH₂ | H | CH₃ |
| CH₃/CH₃ | H | H-C(=O)-CH₂-C(=O)-OH | H | CH₃ |
| CH₃/CH₃ | H | H-C(=O)-CH₂-NH-C(=O)-CH₃ | H | CH₃ |
| CH₃/CH₃ | H | H-C(=O)-NH-SO₂-CH₃ | H | CH₃ |
| CH₃/CH₃ | H | H-C(=O)-NH-NH-C(=O)-NH₂ | H | CH₃ |
| CH₃/CH₃ | H | H-C(=O)-NH-CH₂-CH₂-NH₂ | H | CH₃ |
| CH₃/CH₃ | H | H-C(=O)-CH₂-(3,4-dihydroxyphenyl) | H | CH₃ |
| H/H | H | H-C(=O)-(3,4-dihydroxyphenyl) | CH₃ | H |

-continued

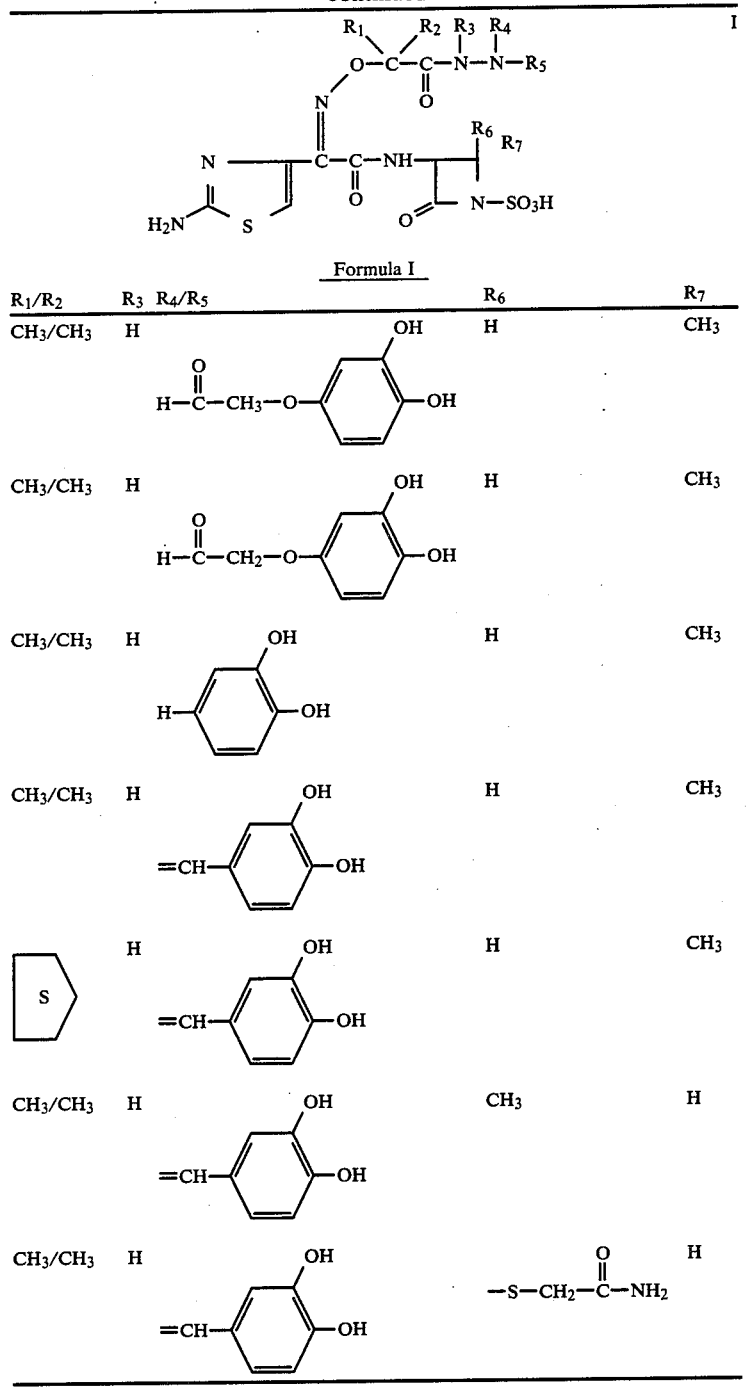

Formula I

| $R_1/R_2$ | $R_3$ | $R_4/R_5$ | $R_6$ | $R_7$ |
|---|---|---|---|---|
| CH₃/CH₃ | H | H-C(=O)-CH₃-O-[3,4-(OH)₂-phenyl] | H | CH₃ |
| CH₃/CH₃ | H | H-C(=O)-CH₂-O-[3,4-(OH)₂-phenyl] | H | CH₃ |
| CH₃/CH₃ | H | H-[3,4-(OH)₂-phenyl] | H | CH₃ |
| CH₃/CH₃ | H | =CH-[3,4-(OH)₂-phenyl] | H | CH₃ |
| (cyclo-S ring) | H | =CH-[3,4-(OH)₂-phenyl] | H | CH₃ |
| CH₃/CH₃ | H | =CH-[3,4-(OH)₂-phenyl] | CH₃ | H |
| CH₃/CH₃ | H | =CH-[3,4-(OH)₂-phenyl] | -S-CH₂-C(=O)-NH₂ | H |

What is claimed is:

1. A compound having the formula

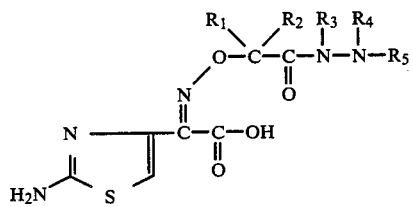

wherein $R_1$ and $R_2$ are each independently hydrogen or alkyl of 1 to 4 carbon atoms, or $R_1$ and $R_2$ together with the carbon atom to which they are attached form a cycloalkyl ring;

$R_3$ is hydrogen or alkyl;

$R_4$ is hydrogen or alkyl, and $R_5$ is hydrogen, alkyl, phenyl, substituted phenyl, phenylalkyl, (substituted phenyl)alkyl, $$-\overset{O}{\underset{\|}{C}}-NHY_1, \quad -\overset{S}{\underset{\|}{C}}-NHY_1, \quad -\overset{O}{\underset{\|}{C}}-Y_2, \quad -\overset{S}{\underset{\|}{C}}Y_2, \quad -\overset{NH}{\underset{\|}{C}}-Y_3,$$

$-SO_2-Y_4$, $-SO_3H$ or $-\overset{\overset{O}{\|}}{\underset{OY_6}{P}}-OY_5$, or together $R_4$ and $R_5$ are =CH-$Y_7$; wherein $Y_1$ is hydrogen, alkyl, phenyl, substituted phenyl, methylcarbonyl, trifluoromethylcarbonyl, phenylcarbonyl, (substituted phenyl)carbonyl, carboxymethyl, methylsulfonyl, phenylsulfonyl, (substituted phenyl)sulfonyl, aminocarbonyl, aminocarbonylamino, aminoethyl, hydroxy, alkoxy, amino, alkyamino, dialkyamino, phenylcarbonylamino, (substituted phenyl)carbonylamino, 1-pyrrolidinyl or 1-piperidinyl; $Y_2$ is hydrogen, alkyl, phenyl, substituted phenyl, alkoxy, formyl, carbonyl, aminocarbonyl, aminothiocarbonyl, methylaminocarbonyl, methylaminothiocarbonyl, trifluoromethyl, phenylmethyl, (substituted phenyl)methyl, phenyloxymethyl, (substituted phenyl)oxymethyl, cyanomethyl, hydroxmethyl, alkoxymethyl, aminomethyl, methylcarbonylaminomethyl, aminocarbonylaminomethyl, methylsulfonylaminomethyl, carboxymethyl, aminocarbonylmethyl, alkoxycarbonylmethyl, hydroxyaminocarbonylmethyl, or azidomethyl;

$Y_3$ is amino, alkyl, alkylthio, carboxythio, alkoxycarbonylthio or aminocarbonylthio;

$Y_4$ is alkyl, amino, hydroxyamino, alkoxyamino, methylcarbonylamino, or phenylcarbonylamino;

$Y_5$ is hydrogen or alkyl;

$Y_6$ is hydrogen, alkyl, carboxymethyl, or aminocarbonylmethyl; and $Y_7$ is phenyl or substituted phenyl;

wherein the terms "alkyl" and "alkoxy" refer to groups having 1 to 10 carbon atoms;

the term "cycloalkyl" refers to cycloalkyl groups having 3, 4, 5, 6 or 7 carbon atoms;

the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms, or carboxyl groups.

2. A compound in accordance with claim 1 wherein $R_3$ and $R_4$ are each hydrogen.

3. A compound in accordance with claim 2 wherein $R_1$ and $R_2$ are each methyl.

4. A compound in accordance with claim 1 wherein $R_1$ and $R_2$ are each methyl.

* * * * *